United States Patent
Lehner et al.

(10) Patent No.: US 9,233,910 B2
(45) Date of Patent: Jan. 12, 2016

(54) PROCESS FOR PURIFYING ANILINE FROM GAS PHASE HYDROGENATIONS

(75) Inventors: Peter Lehner, Baytown, TX (US); Knut Sommer, Krefeld (DE); Amgad Salah Moussa, Köln (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 85 days.

(21) Appl. No.: 13/878,190

(22) PCT Filed: Oct. 17, 2011

(86) PCT No.: PCT/EP2011/068122
§ 371 (c)(1),
(2), (4) Date: Oct. 28, 2013

(87) PCT Pub. No.: WO2012/052407
PCT Pub. Date: Apr. 26, 2012

(65) Prior Publication Data
US 2014/0046096 A1    Feb. 13, 2014

(30) Foreign Application Priority Data

Oct. 21, 2010  (DE) .......................... 10 2010 042 731

(51) Int. Cl.
| C07C 209/00 | (2006.01) |
| C07C 209/86 | (2006.01) |
| C07C 209/84 | (2006.01) |

(52) U.S. Cl.
CPC ............. *C07C 209/86* (2013.01); *C07C 209/84* (2013.01)

(58) Field of Classification Search
CPC combination set(s) only.
See application file for complete search history.

(56) References Cited

U.S. PATENT DOCUMENTS

| 2,174,008 | A | * | 9/1939 | Mow ............................... 203/91 |
| 5,808,157 | A | | 9/1998 | Langer et al. |
| 5,877,350 | A | | 3/1999 | Langer et al. |
| 7,692,042 | B2 | | 4/2010 | Dugal et al. |
| 2005/0080294 | A1 | | 4/2005 | Renner et al. |
| 2007/0203364 | A1 | | 8/2007 | Dugal et al. |
| 2007/0238901 | A1 | | 10/2007 | Dugal et al. |
| 2008/0234518 | A1 | | 9/2008 | Sommer et al. |
| 2009/0065347 | A1 | | 3/2009 | Sommer et al. |
| 2013/0327086 | A1 | * | 12/2013 | Moussa et al. .................. 62/617 |

FOREIGN PATENT DOCUMENTS

| CN | 101024615 | | 8/2007 |
| DE | 10 2006 007 619 | A1 | 8/2007 |
| DE | 10 2007 039 091 | A1 | 2/2009 |
| EP | 0696573 | A1 | 2/1996 |
| EP | 0696574 | A1 | 2/1996 |
| EP | 1845079 | A1 | 10/2007 |
| EP | 1845080 | A1 | 10/2007 |

(Continued)

OTHER PUBLICATIONS

German Search Report dated Jul. 13, 2010.

(Continued)

*Primary Examiner* — Clinton Brooks
(74) *Attorney, Agent, or Firm* — Miles & Stockbridge PC

(57) ABSTRACT

The invention relates to a process for purifying aniline produced by gas-phase hydrogenation of nitrobenzene, by fractional condensation of the crude reaction product obtained in gaseous form so that at least two liquid process products, a partial condensate (PK) and a total condensate (TK), are obtained.

16 Claims, 5 Drawing Sheets

(56) References Cited

FOREIGN PATENT DOCUMENTS

| | | |
|---|---|---|
| EP | 1882681 A1 | 1/2008 |
| EP | 2028176 A1 | 2/2009 |
| JP | 49035341 A | 4/1974 |
| JP | 08295654 A | 11/1996 |
| JP | 2005350388 A | 12/2005 |
| JP | 2007217405 A | 8/2007 |

OTHER PUBLICATIONS

International Search Report for PCT/EP2011/068122 Mailed Jan. 20, 2012.

* cited by examiner

PROCESS FOR PURIFYING ANILINE FROM GAS PHASE HYDROGENATIONS

CROSS REFERENCE TO RELATED APPLICATIONS

This application is a §371 National Stage Application of PCT/EP2011/068122, filed Oct. 17, 2011, which claims priority to German Application No. 102010042731.4, filed Oct. 21, 2010.

BACKGROUND

1. Field of the Invention

The invention relates to a process for purifying aniline produced by gas-phase hydrogenation of nitrobenzene, by fractional condensation of the crude reaction product obtained in gaseous form so that at least two liquid process products, a partial condensate (PK) and a total condensate (TK), are obtained, wherein the condensation leading to the formation of PK is carried out at higher condensation than the temperature leading to the formation of TK, a product stream originating from PK and a product stream originating from TK are each passed separately from one another into a distillation column consisting of at least one stripping section and at least one rectifying section, wherein the product stream originating from PK is introduced into the lower section of the distillation column between the lowermost stripping section and the section which follows, and the product stream originating from TK is introduced into the top of the distillation column above the uppermost rectifying section, and the desired purified aniline is withdrawn in a side stream between the lowermost stripping section and the uppermost rectifying section of the distillation column.

2. Description of Related Art

Aromatic amines are important intermediates, which must be available inexpensively and in large amounts. Aniline, an aromatic amine which is of particular importance industrially, can be purified in an outstanding manner by the process according to the invention. Aniline is an important intermediate in the production of di- and poly-isocyanates of the diphenylmethane series (MDI) and is produced on an industrial scale generally by catalytic hydrogenation of nitrobenzene. Installations with very large capacities must be constructed for that purpose in order to be able to cover the enormous worldwide requirement. The hydrogenation of nitrobenzene is preferably carried out in the gas phase on stationary, heterogeneous supported catalysts, such as, for example, Pd on aluminium oxide or carbon supports, in fixed-bed reactors at an absolute pressure of from 2 to 50 bar and a temperature in the range from 250 to 500° C. under adiabatic conditions in gas recycle mode; see EP-A-0 696 573, EP-A-0 696 574 and EP-A-1 882 681. "Gas recycle mode" means that the non-condensable gases (that is to say substantially hydrogen not reacted during the hydrogenation and any added inert gases) contained in the crude reaction product, optionally with the exception of small amounts diverted off to keep constant further gaseous components of the recycle gas—such as, for example, ammonia formed on the catalyst by deamination reactions, are fed back into the reaction.

In the production of aniline, water and organic secondary products are also formed in addition to the target product. Amounts of unreacted nitrobenzene may additionally also be present, depending upon the production process. Such organic secondary components, as well as any unreacted nitrobenzene, must be separated off before the aniline is used further. The organic secondary components and any unreacted nitrobenzene can be divided into two groups: a) the group of the "low boilers", that is to say compounds or azeotropically boiling mixtures of individual components having boiling points below that of aniline (b.p.=184° C.), and b) the group of the "high boilers", that is to say compounds or azeotropically boiling mixtures of individual components having boiling points above that of aniline. Nitrobenzene (b.p.=211° C.) accordingly belongs to the group of the high boilers.

A crude product stream of a gas-phase hydrogenation installation of nitrobenzene accordingly generally comprises:
aniline,
process water (i.e. the sum of water formed in the reaction and water optionally added to the starting gas stream),
non-condensable gases (excess hydrogen—optionally containing gaseous impurities such as, for example, methane, carbon oxides—and optionally added inert gases, for example for improving the selectivity of added nitrogen, see EP-A-1 882 681, and optionally gaseous secondary products, for example ammonia from deamination reactions),
low boilers, and
high boilers (which can optionally also contain amounts of unreacted nitrobenzene).

An example of the group of the low boilers is benzene (b.p.=80° C.), and an example of the group of the high boilers is diphenylamine (b.p.=302° C.). The aniline can easily be separated from those two impurities mentioned as examples because their boiling points are very different from that of aniline ($\Delta T_s$=104 K and 118 K). On the other hand, it is precisely the high boilers which, after condensation of the product, make it necessary to evaporate and condense the aniline again, so that their presence is particularly problematical.

A particular difficulty is in addition the separation of those secondary products whose boiling points are very similar to those of aniline, because the outlay in terms of distillation is considerable here. In this context, the separation of phenol (b.p.=182° C.) represents a major challenge for distillation technology, which is reflected in the use of long distillation columns with a large number of plates and high reflux ratios, with a correspondingly high outlay in terms of investment and energy.

Compounds having phenolic hydroxy groups, that is to say compounds that carry at least one hydroxy group (—OH) directly on an aromatic ring, can generally be problematical in the working-up of aniline. In addition to phenol, which has already been mentioned, particular mention may be made of the various aminophenols.

The purification of aniline is therefore not a trivial matter and has considerable industrial importance. Many approaches address in particular the mentioned problem in connection with compounds having phenolic hydroxy groups. The solution consists in converting the compounds having phenolic hydroxy groups into the corresponding salts by reaction with suitable bases, the salts, as non-volatile compounds, being substantially easier to separate off.

JP-A-49-035341, US-A-2005 080294, EP-A-1 845 079 and EP-A-2-028 176 accordingly disclose processes in which an aromatic amine is distilled in the presence of a base. In that procedure, problems of solids deposition, fouling and/or a pronounced rise in viscosity in the distillation must be prevented by complex and/or expensive measures.

As an alternative to the removal of compounds having phenolic hydroxy groups from aniline during the distillation, JP-A-08-295654 describes an extraction with dilute aqueous alkali hydroxide solution. Disadvantages of that process are the high NaOH consumption and the formation—as a result of the low concentration of the alkali hydroxide solutions—of very large amounts of waste water containing alkali phenolate.

EP-A-1 845 080 describes a process for the purification of aniline by extraction with aqueous alkali metal hydroxide solution having a concentration >0.7% by mass, wherein the concentration and temperature are so adjusted that the aqueous phase always represents the lower phase in the subsequent phase separation.

JP-A-2007217405 describes a process in which the phenol-containing aniline is brought into contact with aqueous alkali metal hydroxide solution at least twice, in such a manner that the concentration of alkali metal hydroxide in the aqueous phase is from 0.1% by mass to 0.7% by mass.

JP-A-2005 350388 relates very generally to the improvement of aniline working-up. A process is described in which a portion of the bottom product of the aniline distillation column is discharged therefrom and converted into the gas phase separately, that is to say in a second evaporator which is different from the actual evaporator of the column. The gas phase so obtained is fed back into the pure aniline column; high boiler fractions that cannot be evaporated are separated off. A disadvantage of that process is that low boilers and water must be separated off upstream of the actual aniline distillation column by an additional distillation in a dewatering column in a process that is complex in terms of apparatus.

None of the mentioned publications discusses how to reduce the proportion of aniline that must be evaporated and condensed again in a distillation process. If the aniline to be purified is from a gas-phase process, it even passes through two condensations according to the prior art: the reaction product obtained in gaseous form is first condensed as completely as possible, the aqueous phase is separated off, and the resulting organic phase is distilled, that is to say the desired product is (i) condensed, (ii) evaporated and (iii) condensed again, which is very expensive in terms of energy and apparatus and leads to considerable thermal stresses on the aniline.

Accordingly, it was an object of the present invention to provide a process for purifying aniline from gas-phase hydrogenations, in which only a minimal proportion of the aniline itself must be evaporated and condensed again and in which the separation of compounds having phenolic hydroxy groups is achieved as effectively as possible with minimal losses of valuable aniline.

SUMMARY

The object has been achieved by a process for the production of aniline by gas-phase hydrogenation of nitrobenzene and subsequent purification of the aniline, wherein there is obtained a gaseous crude reaction product consisting of aniline, process water, non-condensable gases, low boilers and high boilers, which reaction product is subjected to fractional condensation so that at least two, preferably exactly two, liquid process products, namely at least one, preferably one, partial condensate (PK) and a total condensate (TK), are obtained, wherein
the condensation leading to the formation of PK is carried out at a higher temperature than the condensation leading to the formation of TK, PK comprises the major proportion of the high boilers, while TK comprises the major proportion of the low boilers as well as the major proportion of the aniline and the major proportion of the process water, characterised in that
a product stream originating from PK and a product stream originating from TK are passed into a distillation column comprising at least two sections, namely at least one stripping section (AT) and at least one rectifying section (VT), wherein the product stream originating from PK is introduced into the lower section of the distillation column between the lowermost stripping section and the section which follows, and the product stream originating from TK is introduced into the top of the distillation column above the uppermost rectifying section, and wherein
distilled aniline is withdrawn in a side stream between the lowermost stripping section and the uppermost rectifying section of the distillation column.

DETAILED DESCRIPTION OF A PREFERRED EMBODIMENT

Figure 1:
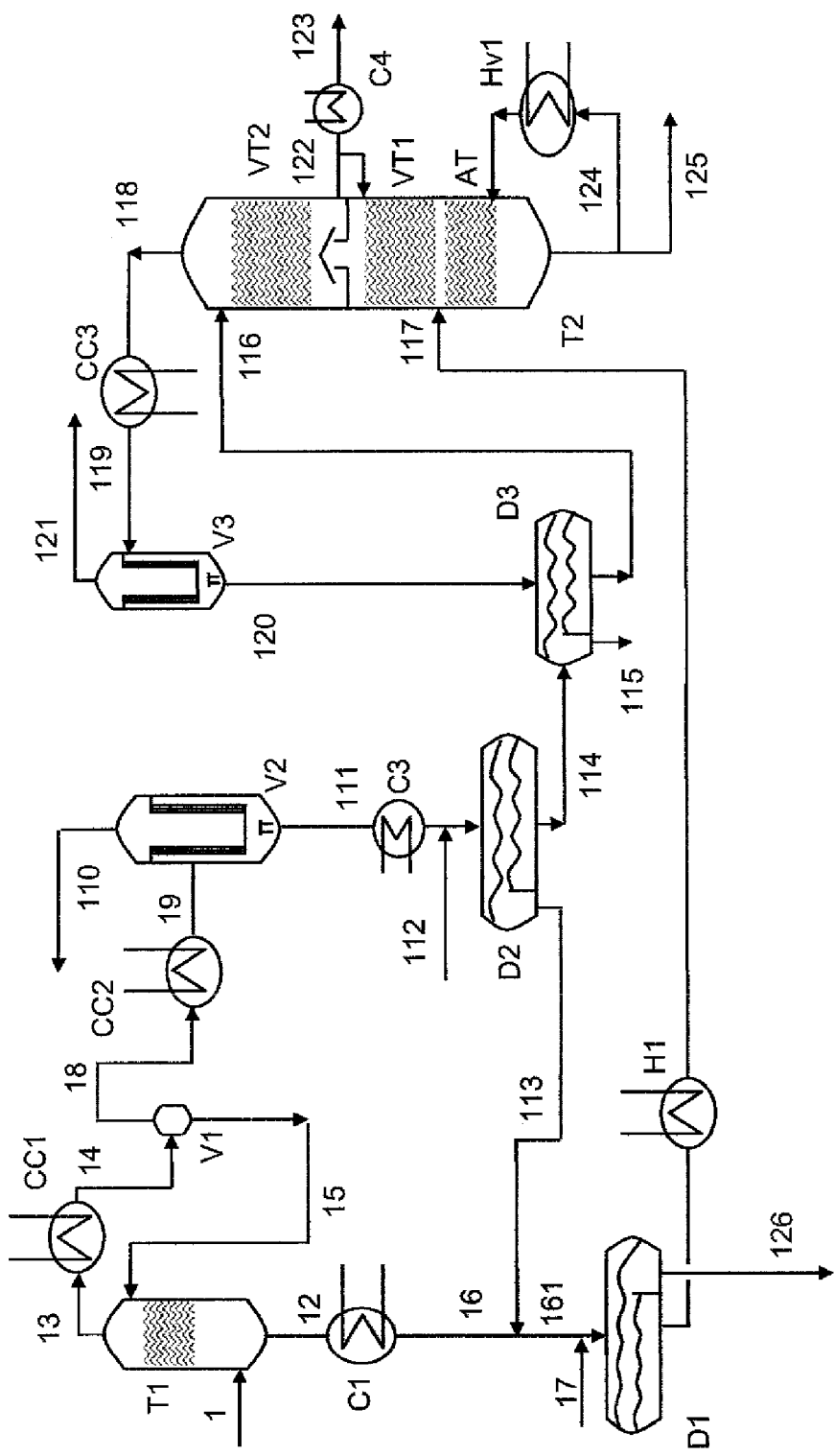
FIGS. 1-5 depict embodiments of the present invention

The process is explained in the following by means of the preferred embodiment, which relates to the formation of exactly two condensate streams (PK and TK). It is a simple matter for the person skilled in the art to modify this process so that it comprises more than two condensate streams, for example by providing a plurality of partial condensation stages $PK_1$, $PK_2$, etc. upstream of the last condensation stage (TK), which is as complete as possible.

In the simplest embodiment of the process according to the invention, the product stream originating from PK is the partial condensate obtained in the fractional condensation, that is to say it is identical with PK itself, and the product stream originating from TK is the organic phase which is obtained by phase separation of TK or of a process product comprising TK, obtained by combining TK with further product streams (see FIG. 4 and the associated explanations), into an aqueous phase and an organic phase.

Depending upon the precise separation task (i.e. ultimately upon the secondary product spectrum, which varies according to the production process), it may be advantageous to treat the aniline with base in order to remove acidic impurities, in particular the mentioned compounds having phenolic hydroxy groups, even more completely than would otherwise be possible. In such a case, the product stream originating from PK is preferably an organic phase which is obtained after mixing PK or a process product comprising PK, obtained by combining PK with further product streams (see FIGS. 1 to 3 and the associated explanations), with aqueous base solution and subsequent phase separation into an aqueous phase and an organic phase. Analogously, the product stream originating from TK is in such a case preferably an organic phase which is obtained after mixing TK or a process product comprising TK (see FIGS. 2 to 3 and the associated explanations) with aqueous base solution and subsequent phase separation into an aqueous phase and an organic phase.

Particularly preferably, in this embodiment PK or the process product comprising PK, before, during or after mixing with aqueous base solution, is additionally mixed in a single- or multi-stage process with water or with a stream A comprising at least 50% by mass water, preferably at least 80% by mass water, particularly preferably at least 90% by mass water, based on the total mass of stream A, in order to reduce the salt load of the product stream originating from PK as far as possible. Most particularly preferably, stream A is an aqueous phase which is obtained after mixing TK or a process product comprising TK with aqueous base solution and subsequent phase separation into an aqueous phase and an organic phase.

It is likewise preferred additionally to mix TK or the process product comprising TK, before, during or after mixing with aqueous base solution (but before phase separation), in a single- or multi-stage process with water or with a stream B comprising at least 50% by mass water, preferably at least 80% by mass water, particularly preferably at least 90% by mass water, based on the total mass of stream B. Alternatively, it is also possible to wash the organic phase obtained after mixing TK or a process product comprising TK with aqueous base solution and subsequent phase separation in a single- or multi-stage process with water or with a stream B comprising at least 50% by mass water, preferably at least 80% by mass water, particularly preferably at least 90% by mass water. In both cases, there is used as stream B preferably a liquid condensate stream of the gas phase removed at the top of the distillation column or a process product comprising a liquid condensate stream of the gas phase removed at the top of the distillation column. A "process product comprising a liquid condensate stream of the gas phase removed at the top of the distillation column" is most particularly preferably a process product that is obtained by adding an aniline-water azeotropic mixture (which is in turn obtained by introducing into a water stripper an aqueous phase obtained by phase separation after mixing PK or a process product comprising PK with aqueous base solution) to the total condensate of the gas phase removed at the top of the distillation column.

Alternatively, the treatment of the aniline with aqueous base solution can also take place after the distillation. In that embodiment, the product stream originating from PK is preferably identical with PK itself, and the product stream originating from TK is preferably the organic phase which is obtained by phase separation of a process product comprising TK (see FIG. 4 and the associated explanations) into an aqueous phase and an organic phase. The aniline withdrawn from the distillation column in a side stream is mixed with aqueous base solution, and an aniline depleted of acidic impurities is obtained by a phase separation.

A distillation column according to the invention comprises at least two sections, a stripping section and a rectifying section. In the simplest case, therefore, the product stream originating from PK is introduced between those two sections, and the product stream originating from TK is passed into the top of the column above the rectifying section. If the distillation column comprises more than two sections, then the product stream originating from PK is preferably introduced between the lowermost stripping section and the section which follows, which is generally a rectifying section. In the case of three sections (see figures), AT (=lowermost stripping section, the only stripping section in this embodiment), VT1 (=rectifying section following AT) and VT2 (=uppermost rectifying section), the product stream originating from TK is introduced between AT and VT1, and the product stream originating from TK is introduced into the top of the column above VT2. The number of sections can also be greater than three.

A possible embodiment of the process according to the invention is explained in greater detail in the following by means of FIG. 1.

In the Figures:

(In this specification, the first number of a reference numeral of a material stream indicates the associated figure. In the case of identical or comparable material streams from different embodiments of the invention, the numbers following the first numbers of the reference numeral in question are the same.)

TABLE 1

Reference numerals of FIG. 1

| Material stream | Meaning | Apparatus | Meaning |
|---|---|---|---|
| 11 | Gaseous crude reaction product (crude aniline) | T1 | Washer for dividing the crude aniline stream into PK and TK |
| 12 | Liquid process product (PK) discharged from T1 | CC1 | Condenser |
| 13 | Top product from T1 | V1 | Separator |
| 14 | 13 after passing through CC1 | CC2 | Condenser |
| 15 | Liquid product stream fed back into the top of T1 | V2 | Separator |
| 16 | 12 after passing through C1 | C3 | Cooler |
| 161 | 16 after mixing with 113 (161 = "process product comprising PK") | D2 | Decanter |
| 17 | Aqueous base solution for treating PK or a process product comprising PK | C1 | Cooler |
| 18 | Top product from V1 | D1 | Decanter |
| 19 | 18 after passing through CC2 | H1 | Preheater |
| 110 | Top product from V2 | D3 | Decanter |
| 111 | Liquid process product (TK) discharged from V2 | T2 | Distillation column |
| 112 | Aqueous base solution for treating TK or a process product comprising TK | AT | Stripping section |
| 113 | Aqueous phase from D2 | VT1 | Upper rectifying section |
| 114 | Organic phase from D2 | VT2 | Middle rectifying section |
| 115 | Aqueous phase from D3 | Hv1 | Evaporator |
| 116 | Organic phase from D3 | C4 | Cooler |
| 117 | Organic phase from D1 | CC3 | Condenser |
| 118 | Gas phase removed at the top of T2 | V3 | Separator |
| 119 | 118 after passing through CC2 (total condensate of 118) | | |
| 120 | Liquid condensate stream removed at the bottom of V3 | | |

TABLE 1-continued

Reference numerals of FIG. 1

| Material stream | Meaning | Apparatus | Meaning |
|---|---|---|---|
| 121 | Top product from V3 | | |
| 122 | Aniline stream from side withdrawal of T2 | | |
| 123 | Aniline stream from side withdrawal of T2 after passing through C4 | | |
| 124 | Recycle stream to the evaporator Hv1 | | |
| 125 | Discharged bottom runnings from T2 | | |
| 126 | Aqueous phase from D1 | | |

The gaseous reaction product, stream 11, consisting of aniline, process water, non-condensable gases, low boilers and high boilers, is first passed into the washer T1. Stream 13 is withdrawn at the top of T1 and cooled in the condenser CC1 to a temperature of from 60° C. to 160° C., preferably from 80° C. to 140° C. and particularly preferably from 100° C. to 120° C. (condensation leading to the formation of PK). The absolute pressure is from 1 bar to 50 bar, preferably from 2 bar to 20 bar and particularly preferably from 2 bar to 10 bar.

The stream 14 so obtained is separated in the separator V1 into a gaseous phase and a liquid phase. The stream 15 fed back into the top of T1 is in this embodiment the liquid phase removed at the bottom of V1. There is thus formed in T1 a liquid process product (PK) enriched with high boilers, which is removed at the bottom (stream 12). As well as comprising the high boilers (preferably from 90% by mass to 100% by mass of the high boilers contained in stream 11), stream 12 (PK) also comprises fractions of aniline (preferably from 0.1% by mass to 35% by mass of the aniline contained in stream 11), of low boilers (preferably <1% by mass of the low boilers contained in stream 11) and of process water (preferably <5% by mass of the process water contained in stream H). Stream 12, preferably after passing through a cooler C1 (then stream 16), is mixed in a single- or multi-stage process with aqueous base solution 17 and with water (not shown) or with a stream A (preferably stream 113) comprising at least 50% by mass, preferably at least 80% by mass, particularly preferably at least 90% by mass, water and fed to the decanter D1. Mixing with water or with a stream comprising at least 50% by mass water can take place before, at the same time as or after mixing with base solution, preferably after.

All water-soluble basic compounds are suitable in principle for the production of the aqueous base solutions according to the invention, such as, for example, alkali metal or alkaline earth metal hydroxides, carbonates or hydrogen carbonates. A solution of sodium hydroxide in water is preferably used as the base solution, the content by mass of sodium hydroxide being preferably at least 10%, particularly preferably at least 20% and most particularly preferably at least 30%, based on the total mass of the sodium hydroxide solution. Extremely particularly preferably, commercially available 32% sodium hydroxide solution is used. The molar ratio of base to the sum of all phenolic hydroxy groups is at least 1:1, but a molar excess of base is preferably used. A molar excess of base to the sum of all phenolic hydroxy groups of not more than 20:1, preferably of not more than 15:1 and particularly preferably of not more than 10:1 is maintained. In the case of multi-stage base treatments, that molar ratio is preferably maintained in each stage. In order to be able to establish the desired molar ratio of base to the sum of all phenolic hydroxy groups, the composition of the process stream that is to be treated must be known. It is determined by conventional analytical methods, preferably by gas chromatography. The details given above relating to the nature and amount of the base that is to be used apply to all embodiments of the process according to the invention. The two-phase process product obtained by base treatment and washing with water is subjected in the decanter D1 to a phase separation known to the person skilled in the art, wherein salts (excess base and salts of the compounds having phenolic hydroxy groups) remain predominantly to completely in the aqueous phase. The aqueous phase (stream 126) is preferably fed to a waster-water treatment, particularly preferably a waste-water stripper.

The gaseous stream 18 removed from the top of V1 is condensed in the condenser CC2 so that a liquid process product (condensation leading to the formation of TK) forms in addition to a residual gas phase. The condensation temperature is governed by economic boundary conditions: too high a temperature leads to undesirable product losses, too low a temperature leads to an unacceptable energy outlay for the condensation. The condensation temperature that is actually chosen therefore represents a compromise and is preferably from 25° C. to 90° C., particularly preferably from 30° C. to 80° C. and most particularly preferably from 40° C. to 70° C. In this process step, not only aniline condenses; water and low boilers also condense, as well as optionally small amounts of entrained high boilers. The absolute pressure is from 1 bar to 50 bar, preferably from 2 bar to 20 bar and particularly preferably from 2 bar to 10 bar.

The stream 19 leaving CC2 is passed into the separator V2 in order to separate the liquid phase and the gaseous phase. The gaseous phase, which contains the excess hydrogen from the reaction, is preferably fed back into the nitroaromatic compound reduction as recycle gas (stream 110). The liquid process product (TK) removed as stream 111, preferably after passing through a further cooler C3, is mixed in a single- or multi-stage process with base solution (stream 112), the same type of base solution as in stream 17 preferably being used and the molar excess of base preferably being the same as in the base treatment of stream 12 or (in the preferred embodiment) stream 16. Analysis of the stream that is to be treated with base preferably takes place by the same method as in the case of stream 12 or (in the preferred embodiment) stream 16. In addition to the major amount of the aniline (preferably from 65% by mass to 99.9% by mass of the aniline contained in stream 11), the major amount of the low boilers (preferably from 99% by mass to 100% by mass of the low boilers contained in stream 11) and the major amount of the process water (preferably from 95% by mass to 100% by mass of the process water contained in stream 11), stream 111 (TK) can also contain small amounts of entrained high boilers (preferably <10% by mass of the high boilers contained in stream 11). The two-phase process product is then subjected in the decanter D2 to a phase separation known to the person skilled in the art. The aqueous phase thereby obtained comprises the salts of the compounds having phenolic hydroxy groups as well as excess base partially to completely. The aqueous phase is discharged from D2 (stream 113). In a particularly preferred embodiment of the process according to the invention, the stream 113 is preferably used as stream A comprising at least 50% by mass water for washing the stream 16 before, during or after the base treatment of stream 16.

The alkaline treatment in the decanter D2 can be carried out as a single- or multi-stage treatment with aqueous base solution 112. The organic phase obtained by the phase separation in D2 is discharged from D2 (stream 114) and preferably, in order to remove also the final residues of salts, washed in a single- or multi-stage process with water (not shown in FIG. 1) or a stream B (=120) comprising at least 50% by mass water, preferably at least 80% by mass water, particularly preferably at least 90% by mass water. The two-phase process product obtained in that manner is subjected in the decanter D3 to a phase separation known to the person skilled in the art. Washing in the decanter D3 can be carried out as a single- or multi-stage washing. The aqueous phase from the washing (stream 115) is discharged in this embodiment and can then preferably be fed to a further process stage (not shown) in which stream 115 is purified further and the aniline contained in that stream is recovered. Aqueous fractions that remain are fed to waste-water disposal.

The distillation column T2 preferably consists of an upper rectifying section, a middle rectifying section and a lower stripping section, as well as an evaporator Hv1.

The product stream originating from PK, which is introduced into the lower section of the distillation column T2 between the lowermost stripping section and the section which follows, is in this embodiment the organic phase obtained in D1. It is preferably heated in the preheater H1 to from 100° C. to 180° C. and then introduced into T2 (stream 117).

The product stream originating from TK, which is introduced into the top of the distillation column T2 above the uppermost rectifying section, is in this embodiment the organic phase obtained in D3 (stream 116). Stream 116 preferably has a temperature of from 30° C. to 60° C.

The aniline is withdrawn from the distillation column as a side stream (122). A portion of the aniline (preferably from 10% by mass to 80% by mass, particularly preferably from 20% by mass to 50% by mass of the stream 122) is preferably fed back into the distillation column in order to maintain the gas stream therein at a level that allows the low boilers to be separated off sufficiently. The portion of the aniline that is not fed back is preferably cooled further in the cooler C4 and withdrawn as a pure aniline stream 123.

The stream 18 withdrawn at the top comprises, in addition to fractions of aniline, low boilers and residual water, because water cannot be separated off completely in the decanters owing to a certain degree of solubility in the organic phase. After passing through the condenser CC3, stream 119 is fed into V3, where a water-rich condensate (stream 120) is removed at the bottom. In a particularly preferred embodiment of the process according to the invention, that water-rich stream 120 is preferably used for washing the stream 114. In that embodiment, therefore, the organic phase obtained after mixing the product stream originating from TK with aqueous base solution and subsequent phase separation is washed in a single- or multi-stage process with water or with a stream comprising at least 50% by mass water. The gas stream (121) removed at the top of V3 is fed to a waste-gas treatment, preferably combustion.

The bottom product of the distillation column T2 is preferably withdrawn partially to completely, fed partially to completely into the evaporator Hv1 (stream 124), where it is evaporated as far as possible, and fed back into the lower section of the column again. Fractions that cannot be evaporated are preferably removed in stream 125. Stream 125 is fed either to disposal, preferably combustion, or to further processing (e.g. in order to obtain further valuable products such as the diphenylamine that is obtained as a secondary component in aniline production).

Figure 2:
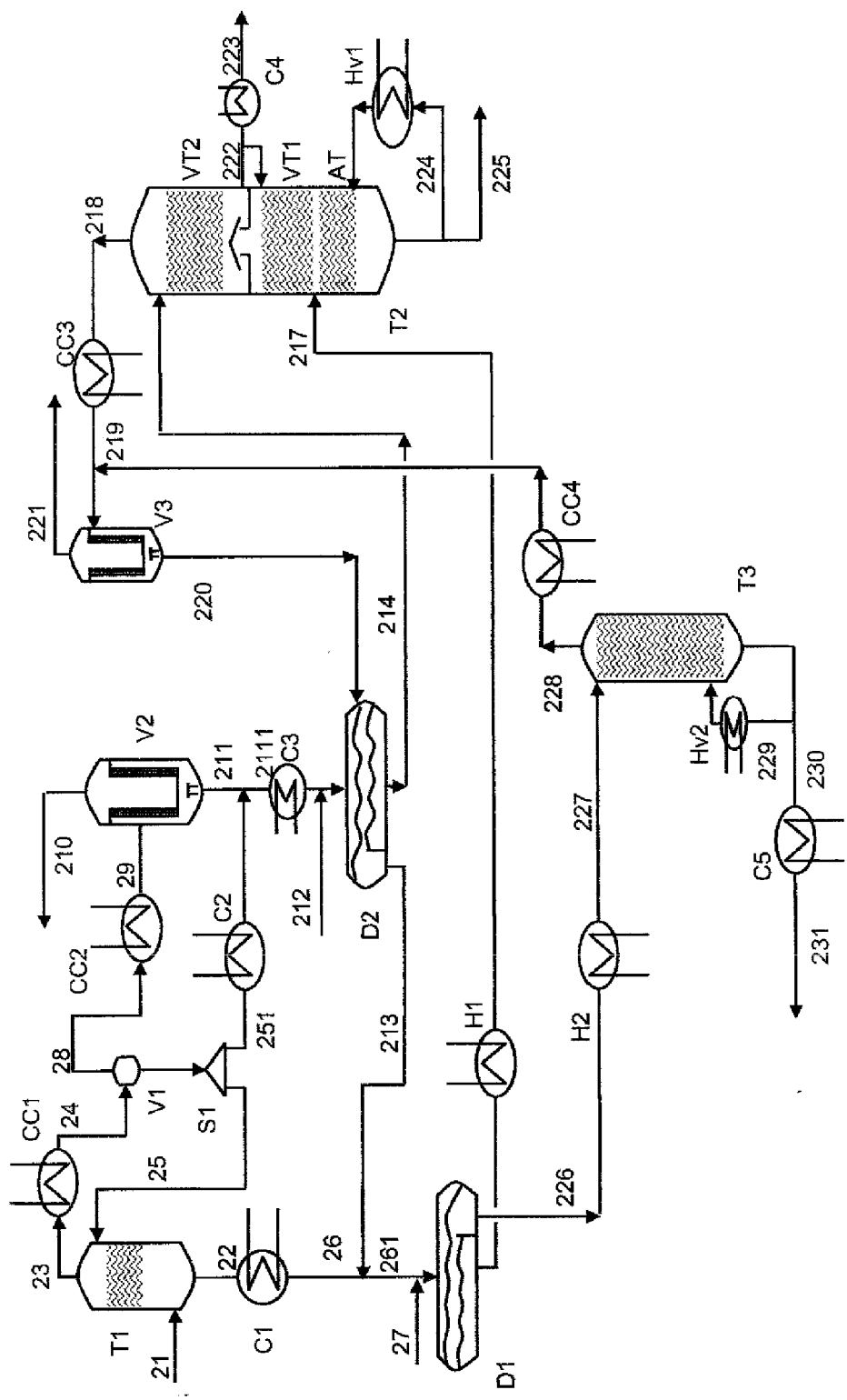

A further preferred embodiment of the process according to the invention is shown in FIG. 2, in which:

TABLE 2

Reference numerals of FIG. 2

| Material stream | Meaning | Apparatus | Meaning |
|---|---|---|---|
| 21 | Gaseous crude reaction product (crude aniline) | T1 | Washer for dividing the crude aniline stream into PK and TK |
| 22 | Liquid process product (PK) discharged from T1 | CC1 | Condenser |
| 23 | Top product from T1 | V1 | Separator |
| 24 | 23 after passing through CC1 | S1 | Splitter |
| 25 | Product stream fed back into the top of T1 | C2 | Cooler |
| 251 | Product stream split in S1 which is not fed back into T1 | CC2 | Condenser |
| 26 | 22 after passing through C1 | V2 | Separator |
| 261 | 26 after mixing with 213 (261 = "process product comprising PK") | C3 | Cooler |
| 27 | Aqueous base solution for the treating PK or a process product comprising PK | D2 | Decanter |
| 28 | Top product from V1 | C1 | Cooler |
| 29 | 28 after passing through CC2 | D1 | Decanter |
| 210 | Top product from V2 | H1 | Preheater |
| 211 | Liquid process product (TK) discharged from V2 | T2 | Distillation column |

TABLE 2-continued

Reference numerals of FIG. 2

| Material stream | Meaning | Apparatus | Meaning |
|---|---|---|---|
| 2111 | 211 after mixing with the stream from C2 | AT | Stripping section |
| 212 | Aqueous base solution for the treating TK or a process product comprising TK | VT1 | Upper rectifying section |
| 213 | Aqueous phase from D2 | VT2 | Middle rectifying section |
| 214 | Organic phase from D2 | Hv1 | Evaporator |
| 217 | Organic phase from D1 | C4 | Cooler |
| 218 | Gas phase removed at the top of T2 | CC3 | Condenser |
| 219 | 218 after passing through CC2 | V3 | Separator |
| 220 | Liquid condensate stream removed at the bottom of V3 | H2 | Preheater |
| 221 | Top product from V3 | T3 | Water stripper |
| 222 | Aniline stream from side withdrawal of T2 | Hv2 | Evaporator |
| 223 | Aniline stream from side withdrawal from T2 after passing through C4 | C5 | Cooler |
| 224 | Recycle stream to the evaporator Hv1 | CC4 | Condenser |
| 225 | Discharged bottom runnings from T2 | C5 | Cooler |
| 226 | Aqueous phase from D1 | CC4 | Condenser |
| 227 | 226 after passing through H2 | | |
| 228 | Top product from T3 (aniline-water azeotropic mixture) | | |
| 229 | Recycle stream to the evaporator Hv2 | | |
| 230 | Discharged bottom runnings from T3 | | |
| 231 | 230 after passing through C5 | | |

Unlike the embodiment shown in FIG. 1, the stream removed at the bottom of the separator V1 is here divided in the splitter S1 and only a portion (preferably from 5 to 99% by mass of the stream 9) is fed back into the top of T1 (stream 25). The remaining portion (stream 251), preferably after passing through a cooler C2, is mixed with the liquid process product (TK) removed as stream 211 from V2, and the mixture so obtained (stream 2111), preferably after passing through a cooler C3, is treated with aqueous base solution (212).

The water-rich stream 226 obtained in D1 is not fed to waste-water treatment as in FIG. 1 but, preferably after passing through the preheater H2, is passed into the top of the water stripper T3 (stream 227). In that manner, an aniline-water azeotropic mixture is obtained, which is removed at the top (stream 228), condensed in the condenser CC4 and mixed with stream 219. The bottom runnings from T3 are fed partially via stream 229 to an evaporator Hv2, where they are fed back into the bottom section of T3 again. Waste water that remains (stream 230), after passing through the cooler C5, is disposed of, for example by combustion or in the clarification plant (stream 231). The energy input for the water stripper T3 and the distillation column T2 is preferably provided by means of steam, the steam used for T3 particularly preferably having a lower pressure than that used for T2.

The product stream originating from TK, which is passed into the top of the distillation column T2 above the uppermost rectifying section, is in this embodiment the organic phase obtained in D2 (stream 214). A decanter D3 is not necessary in this embodiment; stream 220 is passed into D2. Stream 214 in this embodiment preferably has a temperature of from 30° C. to 60° C. (analogously to stream 216 in FIG. 1).

Figure 3:
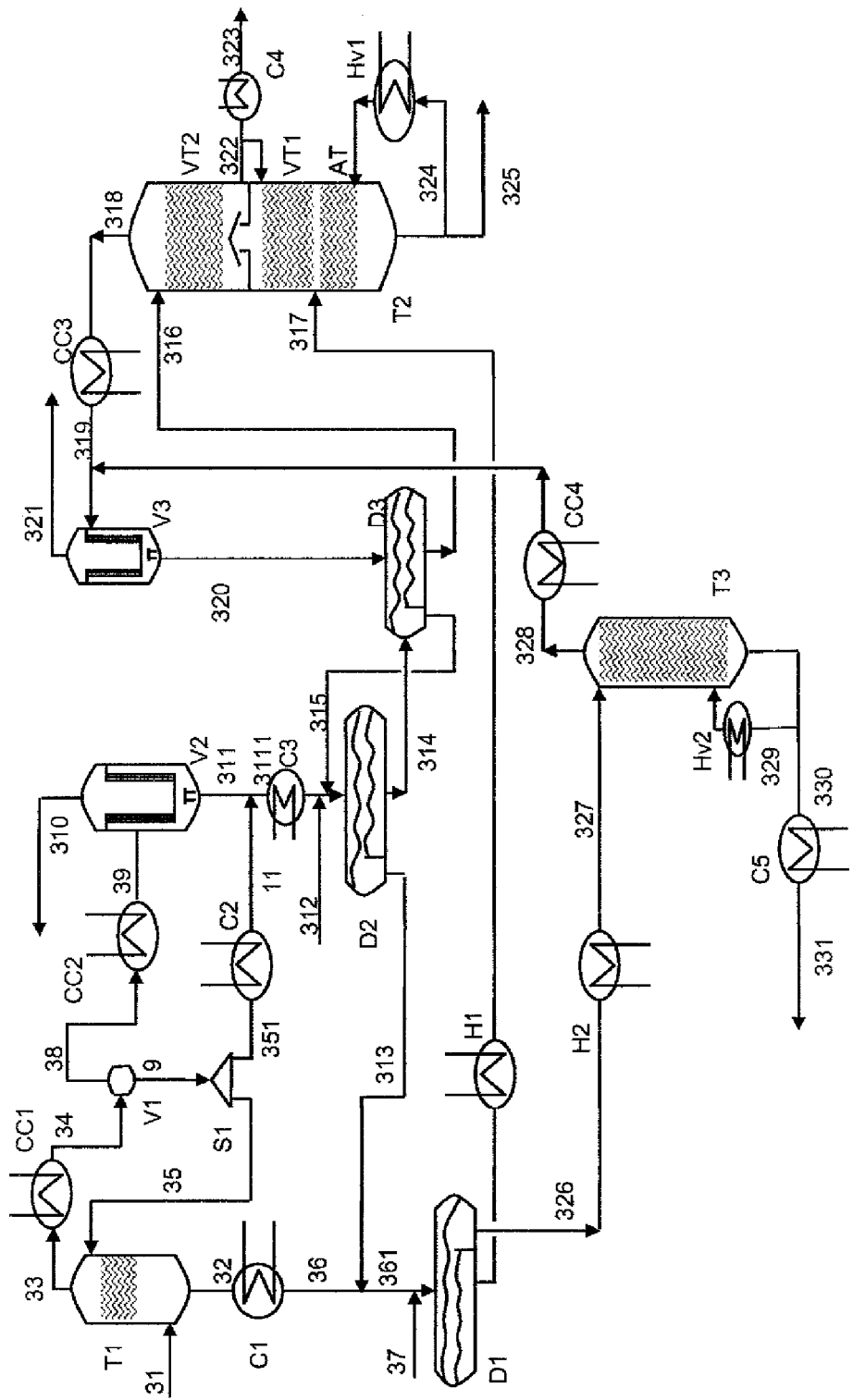

A further preferred embodiment of the process according to the invention in shown in FIG. 3, in which:

TABLE 3

Reference numerals of FIG. 3

| Material stream | Meaning | Apparatus | Meaning |
|---|---|---|---|
| 31 | Gaseous crude reaction product (crude aniline) | T1 | Washer for dividing the crude aniline stream into PK and TK |
| 32 | Liquid process product (PK) discharged from T1 | CC1 | Condenser |
| 33 | Top product from T1 | V1 | Separator |
| 34 | 33 after passing through CC1 | S1 | Splitter |
| 35 | Product stream fed back into the top of T1 | C2 | Cooler |
| 351 | Product stream split in S1 which is not fed back into T1 | CC2 | Condenser |
| 36 | 32 after passing through C1 | V2 | Separator |
| 361 | 36 after mixing with 313 | C3 | Cooler |

TABLE 3-continued

Reference numerals of FIG. 3

| Material stream | Meaning | Apparatus | Meaning |
|---|---|---|---|
| | (361 = "process product comprising PK") | | |
| 37 | Aqueous base solution for treating PK or a process product comprising PK | D2 | Decanter |
| 38 | Top product from V1 | C1 | Cooler |
| 39 | 38 after passing through CC2 | D1 | Decanter |
| 310 | Top product from V2 | H1 | Preheater |
| 311 | Liquid process product (TK) discharged from V2 | D3 | Decanter |
| 3111 | 311 after mixing with the stream from C2 | T2 | Distillation column |
| 312 | Aqueous base solution for treating TK or a process product comprising TK | AT | Stripping section |
| 313 | Aqueous phase from D2 | VT1 | Upper rectifying section |
| 314 | Organic phase from D2 | VT2 | Middle rectifying section |
| 315 | Aqueous phase from D3 | Hv1 | Evaporator |
| 316 | Organic phase from D3 | C4 | Cooler |
| 317 | Organic phase from D1 | CC3 | Condenser |
| 318 | Gas phase removed at the top of T2 | V3 | Separator |
| 319 | 318 after passing through CC2 | H2 | Preheater |
| 320 | Liquid condensate stream removed at the bottom of V3 | T3 | Water stripper |
| 321 | Top product from V3 | Hv2 | Evaporator |
| 322 | Aniline stream from side withdrawal of T2 | C5 | Cooler |
| 323 | Aniline stream from side withdrawal of T2 after passing through C4 | CC4 | Condenser |
| 324 | Recycle stream to the evaporator Hv1 | | |
| 325 | Discharged bottom runnings from T2 | | |
| 326 | Aqueous phase from D1 | | |
| 327 | 326 after passing through H2 | | |
| 328 | Top product from T3 (aniline-water azeotropic mixture) | | |
| 329 | Recycle stream to the evaporator Hv2 | | |
| 330 | Discharged bottom runnings from T3 | | |
| 331 | 330 after passing through C5 | | |

This variant is a combination of those described in FIGS. 1 and 2, in which the stream 314 is washed in the decanter D3 with the runnings from the separator V3 (stream 320). Stream 320 originates in this process variant from the condensates from CC3 and CC4 combined in V3. The washing of stream 314 can be carried out with or without the addition of base, preferably without. In the case of washing with the addition of base (not shown in FIG. 3), the same base as in the base treatment of stream 32 or (in the preferred embodiment) stream 36 is preferably used, but preferably in a considerably smaller quantity and concentration.

Figure 4:
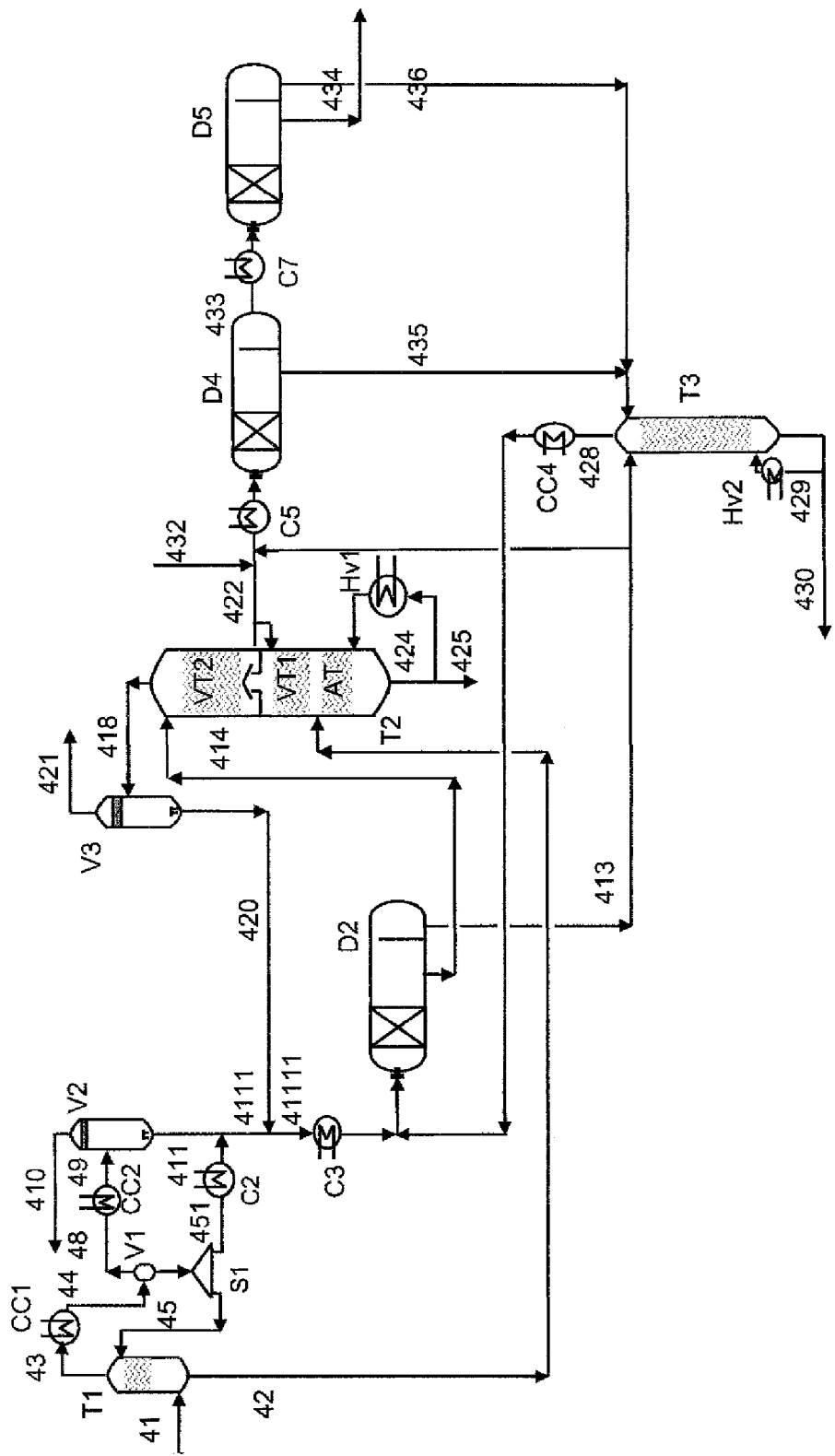

FIG. 4 shows an embodiment of the process according to the invention in which the base treatment takes place after the distillation, in which:

TABLE 4

Reference numerals of FIG. 4

| Material stream | Meaning | Apparatus | Meaning |
|---|---|---|---|
| 41 | Gaseous crude reaction product (crude aniline) | T1 | Washer for dividing the crude aniline stream into PK and TK |
| 42 | Liquid process product (PK) discharged from T1 | CC1 | Condenser |
| 43 | Top product from T1 | V1 | Separator |
| 44 | 43 after passing through CC1 | S1 | Splitter |
| 45 | Product stream fed back into the top of T1 | C2 | Cooler |
| 451 | Product stream split in S1 which is not fed back into T1 | CC2 | Condenser |
| 48 | Top product from V1 | V2 | Separator |

TABLE 4-continued

Reference numerals of FIG. 4

| Material stream | Meaning | Apparatus | Meaning |
|---|---|---|---|
| 49 | 48 after passing through CC2 | C3 | Cooler |
| 410 | Top product from V2 | D2 | Decanter |
| 411 | Liquid process product (TK) discharged from V2 | T2 | Distillation column |
| 4111 | 411 after mixing with the stream from C2 | AT | Stripping section |
| 41111 | 4111 after mixing with 420 | VT1 | Upper rectifying section |
| 413 | Aqueous phase from D2 | VT2 | Middle rectifying section |
| 414 | Organic phase from D2 | Hv1 | Evaporator |
| 418 | Gas phase removed at the top of T2 | V3 | Separator |
| 420 | Liquid condensate stream removed at the bottom of V3 | C5 | Cooler |
| 421 | Top product from V3 | D4 | Decanter |
| 422 | Aniline stream from side withdrawal of T2 | D5 | Decanter |
| 424 | Recycle stream to the evaporator Hv1 | CC4 | Condenser |
| 425 | Discharged bottom runnings from T2 | T3 | Water stripper |
| 428 | Top product from T3 (aniline-water azeotropic mixture) | Hv2 | Evaporator |
| 429 | Recycle stream to the evaporator Hv2 | C7 | Cooler |
| 430 | Discharged bottom runnings from T3 | | |
| 432 | Aqueous base solution | | |
| 433 | Organic phase from D4 | | |
| 434 | Organic phase from D5 (=water-containing purified aniline) | | |
| 435 | Aqueous phase from D4 | | |
| 436 | Aqueous phase from D5 | | |

The product stream originating from PK, which is introduced into the lower section of the distillation column T2 between the lowermost stripping section and the section which follows, is in this embodiment identical with PK itself, that is to say it is the liquid process product discharged as stream 42 from T1. The product stream originating from TK, which is passed into the top of the distillation column T2 above the uppermost rectifying section, is in this embodiment, as in FIG. 2, the organic phase obtained in D2 (stream 414). In this variant of the invention, the aqueous phase from D2 (stream 413) is passed partially to completely into a water stripper (T3) in order to obtain an aniline-water azeotropic mixture (here 428). The aniline-water azeotropic mixture 428, after passing through the condenser CC4, is used for washing the total condensate in the decanter D2.

The bottom runnings of V3 (stream 420) are in this embodiment preferably mixed with stream 4111. The mixture so obtained (stream 41111) is passed into D2 as described above.

Aqueous base solution 432 is added to the distilled aniline 422. The process product so obtained is optionally mixed with aqueous phase from D2 (stream 413) and then, after passing through a cooler C5, passed into the decanter D4, where the acidic impurities are neutralised at temperatures of from 80° C. to 160° C. The aqueous phase from D4 (stream 437) is fed back into the top of T3. The organic phase from D4 (stream 433), which still contains a large amount of water, is passed via a cooler C7 into a further decanter D5 and subjected at from 20° C. to 40° C. to a phase separation in order to reduce the water content of the purified aniline (stream 434) as far as possible. The purified aniline 434 contains substantially only water, corresponding to the solubility of water in aniline at the temperature in the decanter D5. Compounds having phenolic hydroxy groups and other secondary components are present in only insignificant amounts (<100 ppm, preferably <50 ppm, particularly preferably <25 ppm in total, based on the mass of the organic fraction of the stream 434). Depending upon the desired use of the aniline, it can either remain as such or be dried, preferably by stripping (not shown in FIG. 4).

The aqueous phase from D5 (stream 436) is likewise fed back into the top of T3.

The process according to the invention is distinguished from the prior art in that only a portion of the purified aniline has passed through the steps (i) condensation—(ii) evaporation—(iii) condensation again, and not, as is conventional in the prior art, the totality of the purified aniline. In the process according to the invention, only the fraction of the purified aniline that originates from PK has passed through steps (i) to (iii) completely. Only a portion of the fraction of the purified aniline that originates from TK, however, has passed through steps (i) to (iii). The fraction of the aniline contained in the product stream originating from TK and introduced into the top of the column above the uppermost rectifying section, which passes directly into the pure aniline stream, that is to say not via the streams 118/218/318-119/219/319-120/220/320 or 418/420/4111 is not evaporated again after the condensation (i). The fraction of aniline that is not evaporated again is preferably, depending upon the exact boundary conditions, from 65% by mass to 99.9% by mass of the total mass of the pure aniline stream (123/223/323 or 434 after drying). As a result, the outlay in terms of energy and apparatus and the thermal stress on the valuable aniline are reduced significantly.

Furthermore, if required by the particular separation task in question, an effective reduction in the content of compounds having phenolic hydroxy groups in the purified aniline can be achieved in a simple manner by the described base treatment in combination with the described distillation.

The examples which follow describe the purification of a pure aniline which is flowing from a production installation at a mass flow rate of 35,000 kg/h and a temperature of 147° C. and which has the following composition:

TABLE 5

Composition of the crude aniline stream that is to be purified

| Component | Content in % by mass |
|---|---|
| Non-condensable gases | 21.46 |
| Low boilers | 1.140 |

TABLE 5-continued

Composition of the crude aniline stream that is to be purified

| Component | Content in % by mass |
|---|---|
| Water | 25.75 |
| Aniline | 51.51 |
| Phenol | 0.04 |
| High boilers | 0.1 |

In all cases, 32% sodium hydroxide solution was used as the aqueous base solution, in a stoichiometric amount, based on phenol. The distillation is carried out in each case using a column consisting of three sections (from bottom to top: lower stripping section (AT), middle rectifying section (VT1), upper rectifying section (VT2)), which has an evaporator Hv2.

Example 1

Figure 5:
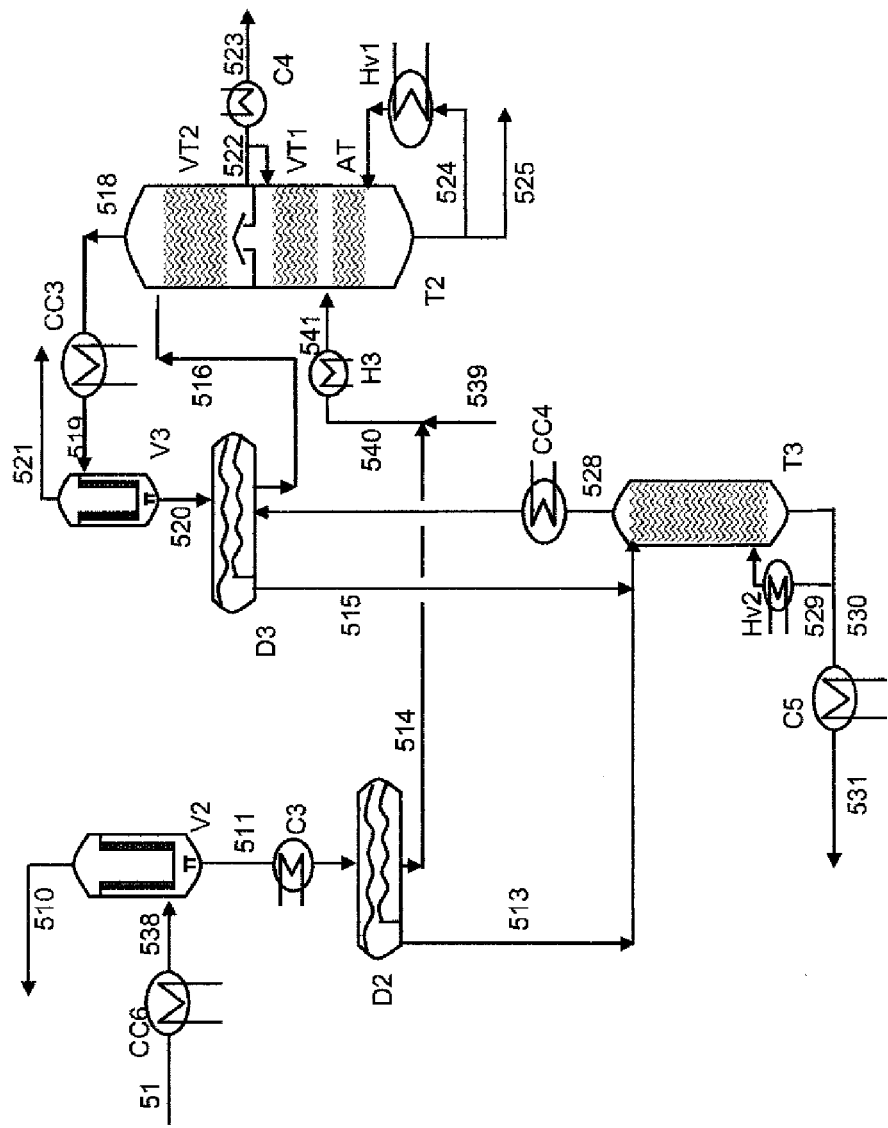

Comparison Example: One Condensation Step, Base is Present During the Distillation. ASPEN Simulation FIG. 5 shows the process used in this example. In the figure:

TABLE 6

| Reference numerals of FIG. 5 | | | |
|---|---|---|---|
| Material stream | Meaning | Apparatus | Meaning |
| 51 | Gaseous crude reaction product (crude aniline) | CC6 | Condenser |
| 510 | Top product from V2 | V2 | Separator |
| 511 | Bottom runnings from V2 | C3 | Cooler |
| 513 | Aqueous phase from D2 | D2 | Decanter |
| 514 | Organic phase from D2 | H3 | Preheater |
| 515 | Aqueous phase from D3 | T2 | Distillation column |
| 516 | Organic phase from D3 | AT | Stripping section |
| 518 | Gas phase removed at the top of T2 | VT1 | Upper rectifying section |
| 519 | Top product from T2 after passing through CC2 | VT2 | Middle rectifying section |
| 520 | Bottom runnings from V3 | Hv1 | Evaporator |
| 521 | Top product from V3 | C4 | Cooler |
| 522 | Aniline stream from side withdrawal of T2 | CC3 | Condenser |
| 523 | Aniline stream from side withdrawal of T2 after passing through C4 | V3 | Separator |
| 524 | Recycle stream to the evaporator Hv1 | D3 | Decanter |
| 525 | Discharged bottom runnings from T2 | T3 | Water stripper |
| 528 | Top product from T3 (aniline-water azeotropic mixture) | Hv2 | Evaporator |
| 529 | Recycle stream to the evaporator Hv2 | C5 | Cooler |
| 530 | Discharged bottom runnings from T3 | CC4 | Condenser |
| 531 | 330 after passing through C5 | | |
| 538 | 51 after passing through CC6 | | |
| 539 | Aqueous base solution | | |
| 540 | Combined streams 514 and 539 | | |
| 541 | 540 after passing through H3 | | |

The following conditions were applied:
Temperature of the gas downstream of CC6 (stream 538): 60° C.
Number of theoretical plates of the upper rectifying section of T2: 10
Number of theoretical plates of the middle rectifying section of T2: 9
Number of theoretical plates of the lower stripping section of T2: 12

In this procedure, the crude aniline stream 51 is not subjected to fractional condensation but is condensed as completely as possible (more than 95% of the aniline) in one step in the condenser CC2. The process product so obtained (511—the "total condensate" of this process) is passed into a separator V2 for recycling of the uncondensed fractions to the hydrogenation process (via stream 510). The entire condensed crude product is cooled further in C3 and then subjected to a phase separation in the decanter D2. Sodium hydroxide solution (539) is supplied to the organic phase 514 so obtained. The NaOH-containing process product 540 so obtained, after passing through a preheater H3, is passed into the distillation column T2 between AT and VT1 (stream 541). Aniline (stream 522) is withdrawn as a side stream between VT2 and VT2 and a portion thereof is fed back into the column again. The fraction that is not fed back is cooled in C4, with the formation of steam, and withdrawn as a pure aniline stream 523. The mass flow of the bottom product, stream 524, is so adjusted that no phenolate salts precipitate in the bottom of T2. The gas phase carried off in T2, stream 518, is cooled to 55° C. in CC3 and passed into a device for separating gases and liquids (V3). The waste gas (stream 521) is fed to combustion. The liquid phase of V3 is separated in the decanter D3 into an aniline-rich phase and a water-rich phase. The aniline-rich phase is introduced into the top of the column T2 (516). The water-rich phases from D2 (stream 13) and D3 (stream 15) are passed into a water stripper (T3), which separates them into a water stream containing less than 100 ppm aniline (529) and a water-aniline azeotropic mixture (528). The latter is condensed in CC4'(V) and fed to D3(V). The results are summarised in Table 7:

TABLE 7

Compositions of the streams and required energy input in Example 1

| | Stream[a] | | |
|---|---|---|---|
| | 510 | 523 | 525 |
| Total mass flow | 10506 kg/h | 16935 kg/h | 736 kg/h |
| Non-condensable gases | 71.42% | 0.00% | 0.00% |
| Low boilers | 3.29% | 75.4 ppm | 0.0 ppm |
| Water | 21.29% | 0.09% | 0.00% |
| Aniline | 4.00% | 99.90% | 93.42% |
| Sum of phenol and sodium phenolate | 9.1 ppm | 0.0 ppm | 2.50% |
| High boilers | 0.00% | 0.0 ppm | 4.08% |
| Temperature | 60° C. | 40° C. | 144° C. |
| Energy input required for T2 | | 5125 kW | |
| Energy input required for T3 | | 3103 kW | |

[a]Contents in % and ppm are always amounts by mass

As can be seen, this procedure involves evaporating the totality of the aniline again in order to separate it from the high boilers. Significant aniline losses via stream 525 also have to be accepted in order to avoid the precipitation of phenolate salts in Hv1. The energy input in T2 is higher than that in D3. That is particularly disadvantageous because steam of a higher pressure is required for the operation of T2 than for the operation of T3. The total energy input required for T2 and T3 is very high at 8228 kW.

Example 2

According to the Invention: Two Condensation Steps, in Each Case a Basic Extraction Before the Distillation. ASPEN Simulation This simulation was carried out on the basis of the process variant already explained in greater detail in FIG. 2 and above. 45% of the liquid condensed in CC1 is passed as stream 5 into the washer T1. The following conditions were applied:

Temperature of the gas downstream of CC1 (stream 24): 118° C.
Number of theoretical plates in T1: 6
Number of theoretical plates of the upper rectifying section of T2: 10
Number of theoretical plates of the middle rectifying section of T2: 10
Number of theoretical plates of the lower stripping section of T2: 11
Temperature in CC2: 60° C.

The results are summarised in Table 8.

TABLE 8

Compositions of the streams and required energy input in Example 2

| | Stream[a] | | |
|---|---|---|---|
| | 210 | 223 | 225 |
| Total mass flow | 9980 kg/h | 17679 kg/h | 62 kg/h |
| Non-condensable gases | 75.17% | 0.00% | 0.00% |
| Low boilers | 3.80% | 20.2 ppm | 0.0 ppm |
| Water | 17.71% | 0.09% | 0.00% |
| Aniline | 3.32% | 99.90% | 51.42% |
| Sum of phenol and sodium phenolate | 9.1 ppm | 4.2 ppm | 0.11% |
| High boilers | 0.00% | 1.7 ppm | 48.47% |
| Temperature | 60° C. | 40° C. | 156° C. |
| Energy input required for T2 | | 1673 kW | |
| Energy input required for T3 | | 3251 kW | |

[a]Contents in % and ppm are always amounts by mass

As can be seen, the use of the process according to the invention leads to a significant reduction both in the energy consumption in T2 and in the aniline losses via stream 225. The total energy consumption in T2 and T3 is only 4924 kW, as compared with 8228 kW in the comparison example. The product quality differs only in that traces of phenolate salts may occur in the product, but still in an acceptable amount. The following example shows how such traces can be reduced to an insignificant value.

Example 3

According to the Invention: Two Condensation Steps, in Each Case a Basic Extraction and Neutral Washing Before the Distillation. ASPEN Simulation This simulation was carried out on the basis of the process variant described in FIG. 3 and already explained above. The other conditions are the same as in Example 2. The results are summarised in Table 9.

TABLE 9

Compositions of the streams and required energy input in Example 3

| | Stream[a] | | |
|---|---|---|---|
| | 310 | 323 | 325 |
| Total mass flow | 9980 kg/h | 17679 kg/h | 62 kg/h |
| Non-condensable gases | 75.17% | 0.00% | 0.00% |
| Low boilers | 3.80% | 19.0 ppm | 0.0 ppm |

TABLE 9-continued

Compositions of the streams and required energy input in Example 3

| | Stream[a] | | |
|---|---|---|---|
| | 310 | 323 | 325 |
| Water | 17.71% | 0.09% | 0.00% |
| Aniline | 3.32% | 99.90% | 51.44% |
| Sum of phenol and sodium phenolate | 9.1 ppm | 0.1 ppm | 0.10% |
| High boilers | 0.00% | 1.7 ppm | 48.47% |
| Temperature | 60° C. | 40° C. | 156° C. |
| Energy input required for T2 | | 1659 kW | |
| Energy input required for T3 | | 3332 kW | |

[a]Contents in % and ppm are always amounts by mass

As can be seen, the pure aniline stream 323 is now virtually free of phenol and phenolate impurities. The total energy consumption in T2 and T3 is only 4991 kW, compared with 8228 kW in the comparison example.

Example 4

According to the Invention: Two Condensation Steps, in Each Case a Basic Extraction and Neutral Washing Before the Distillation, Smaller Distillation Column. ASPEN Simulation This simulation was likewise carried out on the basis of the process described in FIG. 3. In this example, column T2 has fewer plates.
Number of theoretical plates of the upper rectifying section of T2: 9
Number of theoretical plates of the middle rectifying section of T2: 6
Number of theoretical plates of the lower stripping section of T2: 2

The remaining parameters are the same as in Example 3.

The background to this example is to show that the number of plates in T2 is a variable which can be optimised. The process according to the invention especially allows the number of plates to be reduced and accordingly the production and fixed costs also to be lowered.

The results are summarised in Table 10.

TABLE 10

Compositions of the streams and required energy input in Example 4

| | Stream[a] | | |
|---|---|---|---|
| | 310 | 323 | 325 |
| Total mass flow | 9980 kg/h | 17679 kg/h | 62 kg/h |
| Non-condensable gases | 75.17% | 0.00% | 0.00% |
| Low boilers | 3.80% | 19 ppm | 0.5 ppm |
| Water | 17.71% | 0.09% | 0.00% |
| Aniline | 3.32% | 99.90% | 51.46% |
| Sum of phenol and sodium phenolate | 9.1 ppm | 0.1 ppm | 0.09% |
| High boilers | 0.00% | 0.8 ppm | 48.44% |
| Temperature | 60° C. | 40° C. | 156° C. |
| Energy input required for T2 | | 1659 kW | |
| Energy input required for T3 | | 3333 kW | |

[a]Contents in % and ppm are always amounts by mass

As can be seen, the lower number of plates is entirely sufficient. The content of high boilers in the pure aniline stream 323 is even reduced as compared with Example 3. The total energy consumption in T2 and T3 is only 4992 kW, compared with 8228 kW in the comparison example.

The invention claimed is:

1. A process for producing aniline by gas-phase hydrogenation of nitrobenzene and subsequent purification of the aniline, comprising:
    obtaining a gaseous crude reaction product, which is subjected to fractional condensation such that at least two liquid process products are obtained, wherein the at least two liquid process products include at least one partial condensate (PK) and a total condensate (TK),
    carrying out a condensation leading to the formation of PK at a temperature that is higher than the condensation temperature leading to the formation of TK,
    passing a product stream originating from PK and a product stream originating from TK into a distillation column comprising at least two sections, comprising at least one stripping section and at least one rectifying section,
    introducing the product stream originating from PK into a lower section of the distillation column between a lowermost stripping section and a section which follows, and introducing the product stream originating from TK into a top portion of the distillation column above an uppermost rectifying section, and
    withdrawing distilled aniline in a side stream between the lowermost stripping section and the uppermost rectifying section of the distillation column.

2. The process according to claim 1, wherein:
    the condensation leading to the formation of PK is carried out at a temperature from 60° C. to 160° C., and
    the condensation leading to the formation of TK is carried out at a temperature from 25° C. to 90° C.

3. The process according to claim 2, wherein:
    product stream originating from PK is a partial condensate obtained in fractional condensation, and
    product stream originating from TK is an organic phase which is obtained by phase separation of TK and/or a process product comprising TK into an aqueous phase and an organic phase.

4. The process according to claim 2, wherein:
    product stream originating from PK is an organic phase which is obtained after mixing PK and/or a process product comprising PK with aqueous base solution and subsequent phase separation into an aqueous phase and an organic phase, and
    product stream originating from TK is an organic phase which is obtained after mixing TK and/or a process product comprising TK with aqueous base solution and subsequent phase separation into an aqueous phase and an organic phase.

5. The process according to claim 1, wherein:
    product stream originating from PK is a partial condensate obtained in a fractional condensation, and
    product stream originating from TK is an organic phase which is obtained by phase separation of TK and/or a process product comprising TK into an aqueous phase and an organic phase.

6. The process according to claim 5, wherein aniline withdrawn from the distillation column in a side stream is mixed with aqueous base solution, and an aniline depleted of acidic impurities is obtained by phase separation.

7. The process according to claim 1, wherein:
product stream originating from PK is an organic phase which is obtained after mixing PK and/or a process product comprising PK with aqueous base solution and subsequent phase separation into an aqueous phase and an organic phase, and
product stream originating from TK is an organic phase which is obtained after mixing TK and/or a process product comprising TK with aqueous base solution and subsequent phase separation into an aqueous phase and an organic phase.

8. The process according to claim 7, wherein:
PK and/or the process product comprising PK is mixed, before, during and/or after mixing with aqueous base solution, in a single- or multi-stage process with water and/or with a stream A comprising at least 50% by mass water, based on the total mass of stream A.

9. The process according to claim 8, wherein:
stream A comprising at least 50% by mass water is an aqueous phase which is obtained after mixing TK and/or a process product comprising TK with aqueous base solution and subsequent phase separation into an aqueous phase and an organic phase.

10. The process according to claim 7, wherein:
the organic phase obtained after mixing TK and/or a process product comprising TK with aqueous base solution and subsequent phase separation is washed in a single- or multi-stage process with water and/or with a stream B comprising at least 50% by mass water, based on the total mass of stream B.

11. The process according to claim 10, wherein:
stream B comprising at least 50% by mass water is a liquid condensate stream of gas phase removed at a top portion of the distillation column and/or a process product comprising a liquid condensate stream of gas phase removed at the top portion of the distillation column.

12. The process according to claim 11, wherein
the process product comprising the liquid condensate stream of the gas phase removed at the top portion of the distillation column is obtained
by adding an aniline-water azeotropic mixture,
obtained by introducing into a water stripper an aqueous phase obtained by phase separation after mixing PK and/or a process product comprising PK with aqueous base solution,
to total condensate of gas phase removed at a top portion of the distillation column.

13. The process according to claim 7, wherein:
TK and/or process product comprising TK is mixed, before, during and/or after mixing with aqueous base solution, in a single- or multi-stage process with water and/or with a stream B comprising at least 50% by mass water, based on the total mass of stream B.

14. The process according to claim 13, wherein
stream B comprising at least 50% by mass water is a process product comprising liquid condensate stream of gas phase removed at a top portion of the distillation column.

15. The process according to claim 14, wherein:
the process product comprising the liquid condensate stream of the gas phase removed at the top portion of the distillation column is obtained
by adding an aniline-water azeotropic mixture,
obtained by introducing into a water stripper an aqueous phase obtained by phase separation after mixing PK and/or a process product comprising PK with aqueous base solution,
to total condensate of gas phase removed at a top portion of the distillation column.

16. The process according to claim 7, wherein the aqueous base solution comprises a solution of an alkali metal hydroxide and/or alkaline earth metal hydroxide.

\* \* \* \* \*